United States Patent
Yewer, Jr.

[11] Patent Number: 5,500,959
[45] Date of Patent: Mar. 26, 1996

[54] SUPPORT BELT WITH HIGH TENSION CINCHING SYSTEM

[76] Inventor: Edward H. Yewer, Jr., 6259 N. Highway 83, Hartland, Wis. 53029

[21] Appl. No.: 189,858

[22] Filed: Feb. 1, 1994

[51] Int. Cl.$^6$ ..................................................... A61F 5/00
[52] U.S. Cl. .................... 602/19; 2/322; 2/311
[58] Field of Search .................... 2/2, 311, 312, 2/336, 338, 321, 322, 95.1, 100.1, 96.1, 101.1, 121; 482/105, 106; 128/95.1, 100.1, 96.1, 101.1, 121.1, 602.19, 121; 182/3, 4; 602/19

[56] References Cited

U.S. PATENT DOCUMENTS

| | | | |
|---|---|---|---|
| 4,273,130 | 6/1981 | Simpson | 2/338 |
| 4,509,214 | 4/1985 | Shea | 2/322 |
| 4,527,289 | 7/1985 | Shea | 2/322 |
| 4,715,364 | 12/1987 | Noguchi | 2/311 |
| 4,782,535 | 11/1988 | Yewer, Jr. et al. | |
| 5,036,864 | 8/1991 | Yewer, Jr. | |
| 5,178,163 | 1/1993 | Yewer, Jr. | |
| 5,232,424 | 8/1993 | Pearson et al. | 2/338 |
| 5,257,419 | 11/1993 | Alexander | 2/338 |

OTHER PUBLICATIONS

Applicant's Exhibit A, page illustrating "Valeo's Low Profile Belt", admitted prior art. 1994.

Primary Examiner—C. D. Crowder
Assistant Examiner—Gloria Hale
Attorney, Agent, or Firm—Quarles & Brady

[57] ABSTRACT

A support belt has a cinching system which incorporates two or more rings and results in a reduction of the force required to secure the belt around a user's waist. An elastomeric material may be deposited on the interior surface of the belt so as to increase the resistance of the belt to turning around the waist when the belt is being tightened.

13 Claims, 4 Drawing Sheets

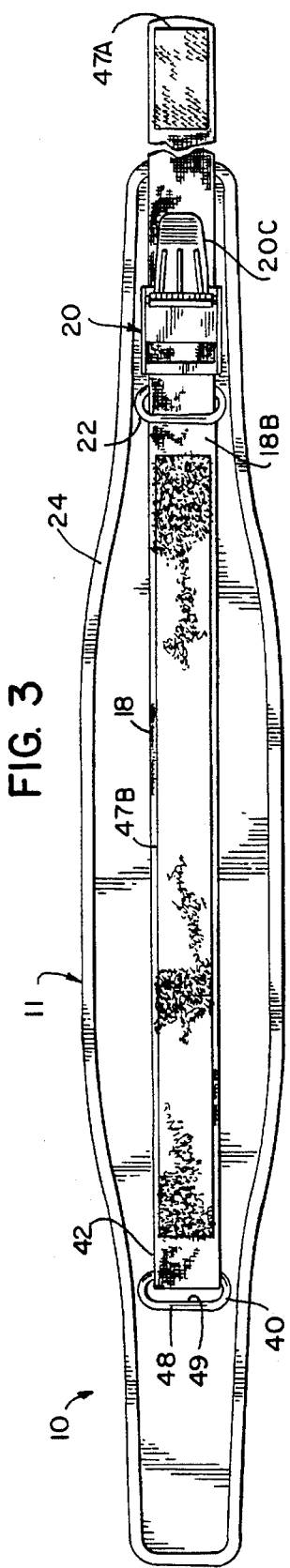
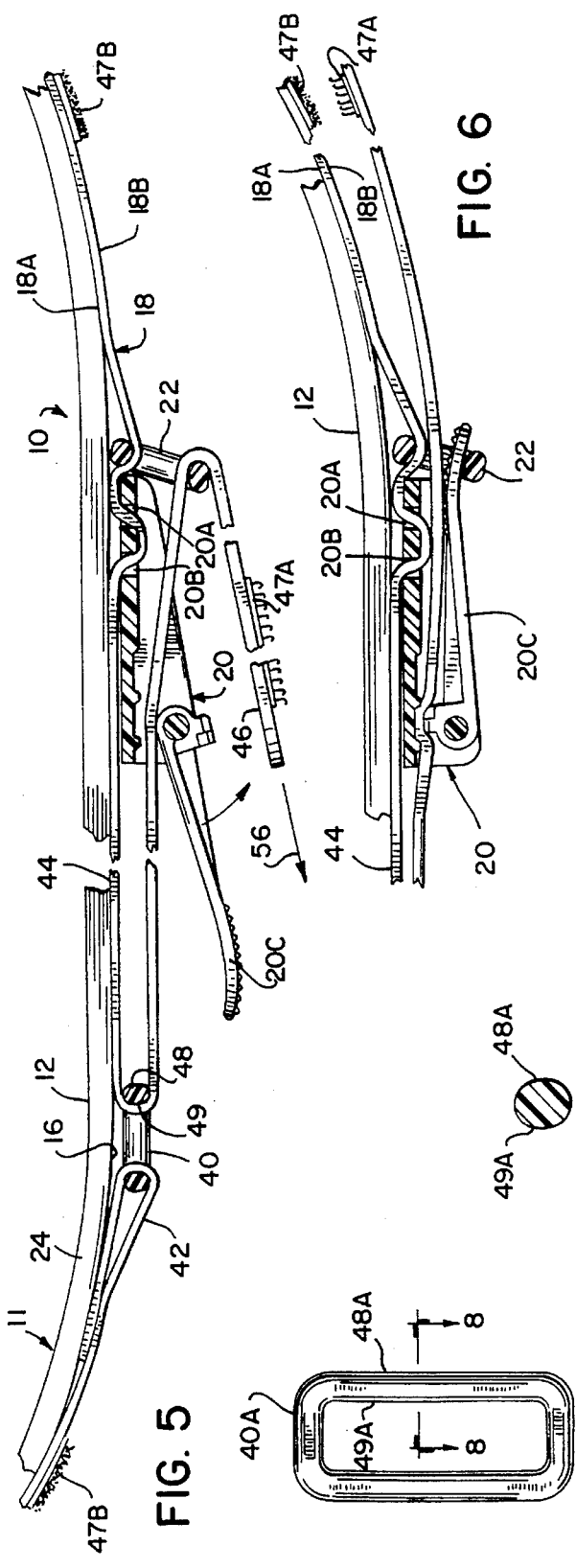

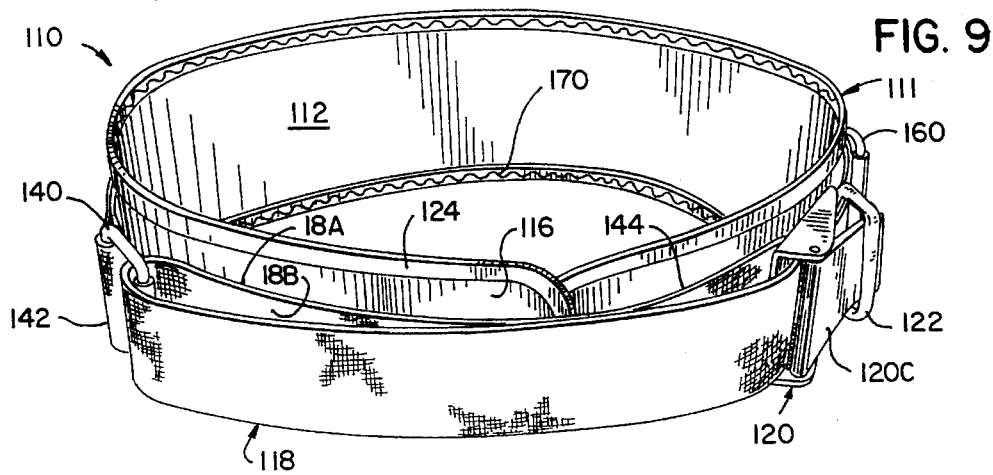
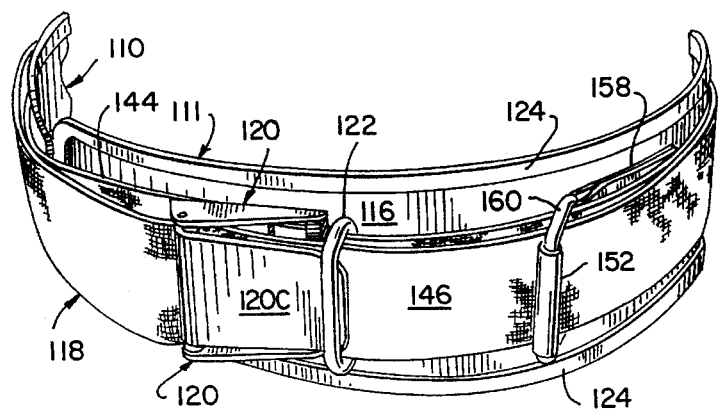
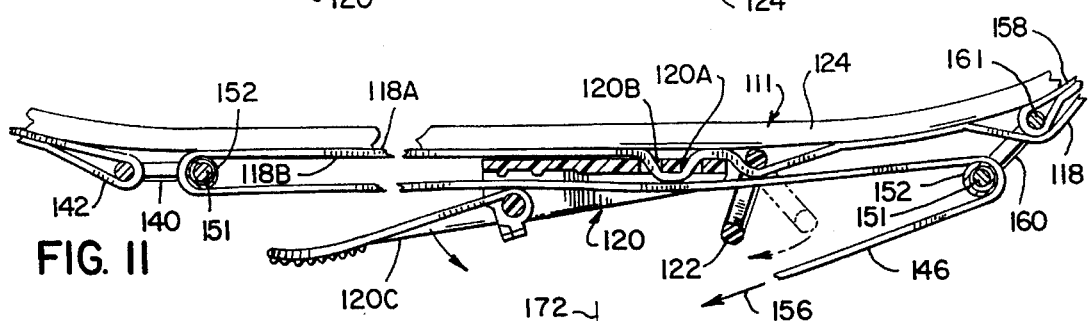
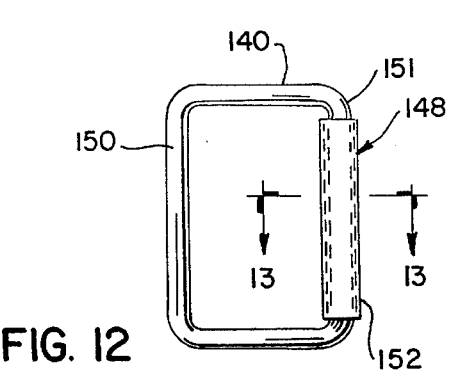
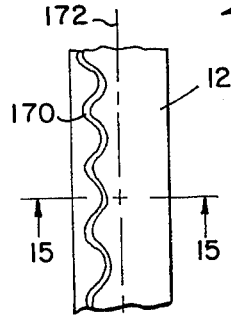
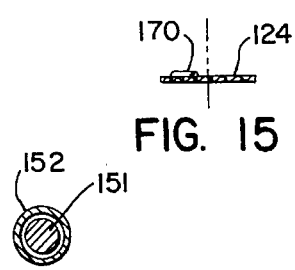

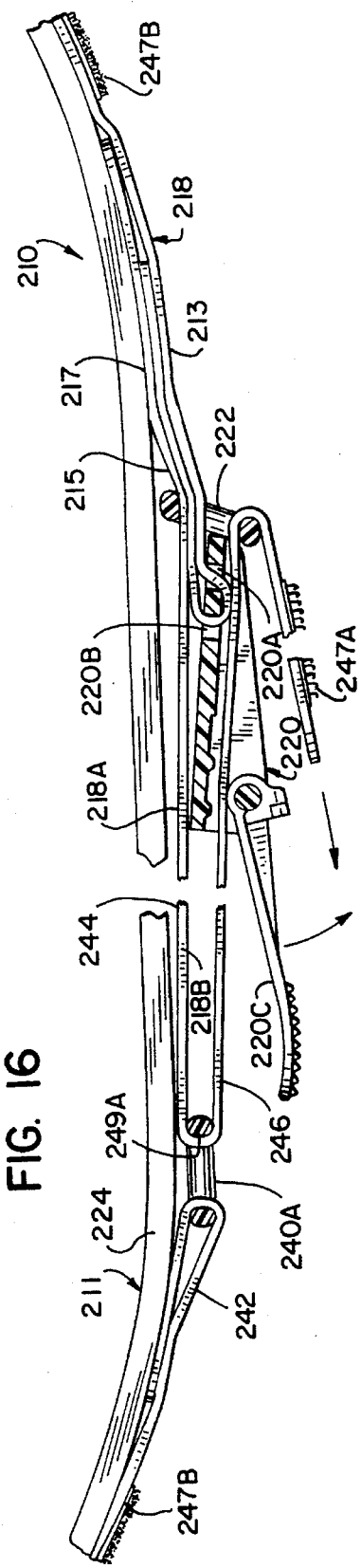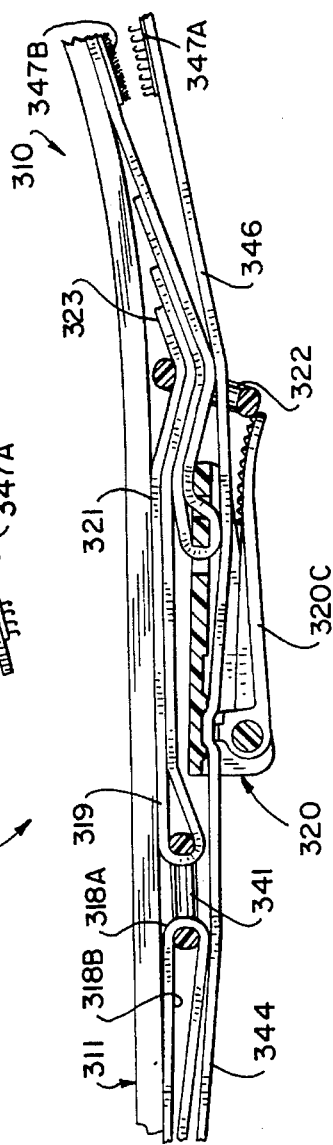
FIG. 16
FIG. 17
FIG. 18

1

SUPPORT BELT WITH HIGH TENSION CINCHING SYSTEM

FIELD OF THE INVENTION

This invention relates to belts of the type that are secured around the waist of a human body, commonly used to enhance the load carrying ability of the body or to relieve or reduce the chance for back stress. In particular, this invention relates to such a belt which can be cinched to a very high tension.

BACKGROUND OF THE INVENTION

It is well known that a support belt may be secured around a human user's waist with the effect of increasing the user's strength and load carrying ability, relieving back pain, and other benefits. Traditionally, support belts have been made of relatively heavy and stiff natural materials, usually leather. An improved belt, made of synthetic materials laminated together is described in U.S. Pat. No. 4,782,535 issued Nov. 8, 1988. In this belt, an inner fabric layer, an intermediate foam layer, and an outer fabric layer are laminated together and a high strength nylon strap is wrapped around the lamination and secured to it.

A buckle-type fastener is provided to secure the ends of the strap so as to hold the belt around the waist of a user. Improved buckle structures for securing such a belt are described in U.S. Pat. No. 5,036,864, issued Aug. 6, 1991, and in U.S. Pat. No. 5,269,050 issued Dec. 14, 1993.

In certain applications, such as heavy weight lifting, the user may like to tighten the belt around his or her waist to a very high tension, so as to create the highest possible intra-abdominal pressure, with a corresponding increase in load bearing ability. This has sometimes required the aid of one or more people in addition to the user to help cinch the belt to the desired tension. While being cinched and while holding such high tensions, the belt and particularly the fastener for holding the belt cinched was subjected to an extraordinary load. The present invention is directed at providing a belt for cinching and holding such high loads.

SUMMARY OF THE INVENTION

The present invention provides a support belt having a strap for surrounding the waist, the strap having an interior surface facing the waist, an exterior surface facing away from the waist, a first end portion and a second end portion opposite from the first end portion, the second end portion having a free end. A power ring is secured to the first end portion, the power ring having an opening therein for receiving the free end therethrough and a bridging portion for contacting the free end on the exterior side of the strap around approximately at least 180° of the bridging portion. A second ring is secured to the second end portion of the strap which has an opening for receiving the free end after the free end is inserted through the power ring and a bridging portion for contacting the free end on the interior surface strap around approximately 180° of the bridging portion. A fastener is adapted to releasably secure the free end after the free end has been inserted through the second ring. Using multiple rings enables applying a higher compressive force to the waist with less tension force on the free end and holding it with the fastener.

In one embodiment, the bridging portion includes a sleeve bearing around a shaft. The sleeve bearing contacts the free end and turns about the shaft when the free end is pulled through the power ring. In this embodiment, most of the sliding when cinching the belt takes place between the sleeve bearing and the shaft, rather than between the free end and the bridging portion, which reduces wear on the strap as it is pulled through the power ring. The frictional forces exerted on the strap by the power ring may also be reduced, especially if the sleeve bearing is properly lubricated or if anti-friction bearings are used between the shaft and the sleeve.

The second ring may be a torque ring which is adjacent to the fastener and can be used to lock the fastener closed, a roller ring having a sleeve bearing as described above, or another power ring. If a roller ring or another power ring is provided as the second ring, a torque ring may also be provided to hold the fastener closed and/or redirect the cinching force. In addition, the fastener can be secured to either the first or the second end of the strap.

In a preferred form, the belt has a body secured adjacent to the interior surface of the strap between the first and second end portions. The body can be made wider than the strap to provide greater axial support and spread the loads exerted by the strap over a larger area, and need not have a high tensile strength as the strap must.

Preferably, the body has an inner surface, which when the belt is in use is adjacent to the waist, having a friction material for increasing the coefficient of friction of the inner surface against the waist. The friction material may be an elastomeric material which is adhered to the inner surface of the body. Preferably, the body includes a binding strip which is folded longitudinally 180° about its longitudinal axis and sewn around the edge of the body, and the friction material is deposited on the binding strip in the area of the binding strip which is on the inner side of the belt. The friction material helps resist turning of the belt around the waist when the belt is being cinched and when the belt is in use.

These and other objects and advantages of the invention will be apparent from the following detailed description and from the drawings.

BRIEF DESCRIPTION OF THE DRAWINGS

FIG. 3 is a plan view of the outer side of the belt of FIG. 1 with the belt laid flat;

FIG. 5 is a partial sectional top view of the belt being cinched;

FIG. 6 is a partial sectional view similar to FIG. 5 but showing the buckle closed;

FIG. 7 is a front plan view showing an alternate embodiment of a power ring for a belt of the invention;

FIG. 8 is a sectional view of the power ring of FIG. 7 as viewed from the plane of the line 8—8 of FIG. 7;

FIG. 9 is a perspective view of an alternate embodiment of a belt of the present invention;

FIG. 10 is a partial perspective view of the belt of FIG. 9 but shown rotated clockwise (as viewed from the top) from the position shown in FIG. 9 to show a different portion of the belt;

FIG. 11 is a view similar to FIG. 5 but showing the embodiment shown in FIGS. 9 and 10;

FIG. 12 is a front plan view of a power ring for the belt of FIGS. 9–11;

FIG. 13 is a sectional view of the power ring shown in FIG. 12 as viewed from the plane of the line 13—13 of FIG. 12;

FIG. 14 is a plan view of a section of binding strip laid flat used to make the belt of FIG. 9;

FIG. 15 is a sectional view through the plane of the line 15—15 of FIG. 14;

FIG. 16 is a view similar to FIG. 5 of another embodiment of a belt of the invention;

FIG. 17 is a view similar to FIG. 5 of another embodiment of a belt of the invention; and FIG. 18 is a fragmentary top plan view of the belt of FIG. 16 with the buckle closed.

DETAILED DESCRIPTION OF THE PREFERRED EMBODIMENTS

Figure 1:
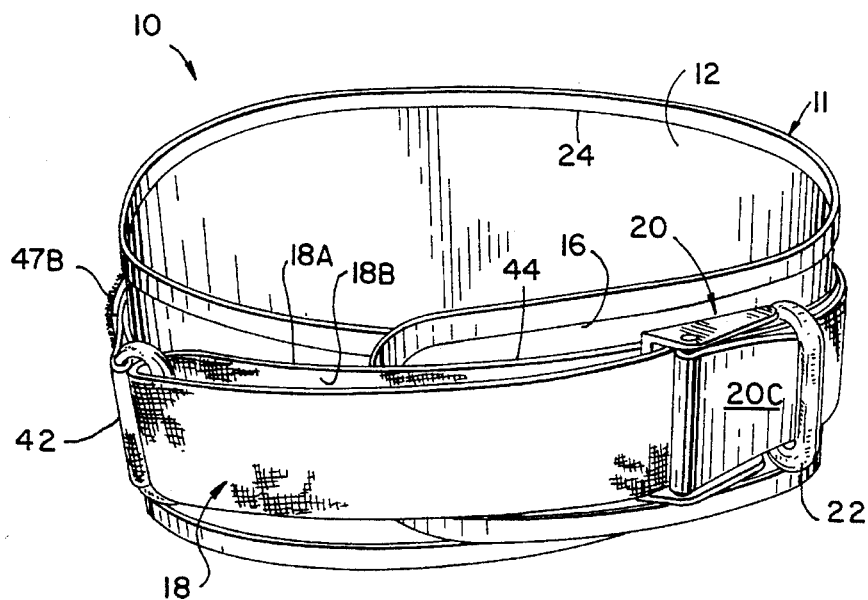
FIG. 1 is a perspective view of a belt of the present invention.
Figure 2:
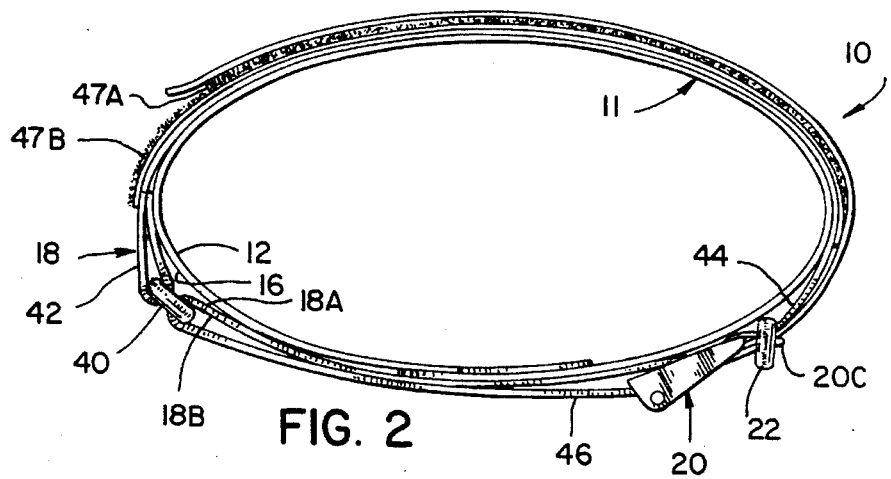
FIG. 2 is a top plan view showing the belt of FIG. 1.
Figure 4:
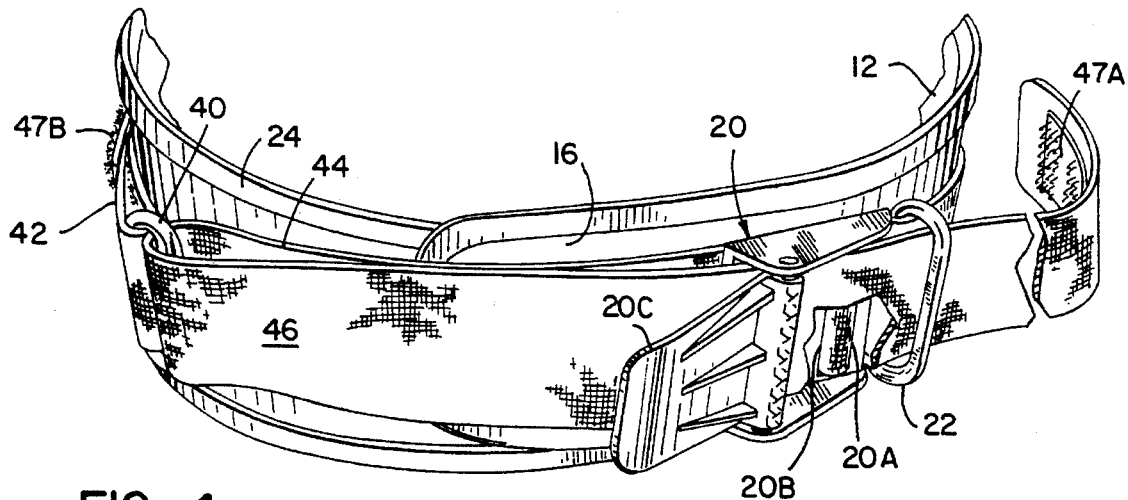
FIG. 4 is a partial perspective view illustrating the belt of FIG. 1 with its buckle open.

Referring to FIG. 1, a support belt 10 of the invention has a body 11 with inner 12 and outer 16 fabric layers laminated to an intermediate foam layer (not shown) and a binding strip 24 stitched around the edge of the lamination. The body 11 may be the same as that described in U.S. Pat. Nos. 4,782,535, 5,036,864 or 5,178,163, the disclosures of which are hereby incorporated by reference, or it may be of any other suitable construction, such as is described in copending commonly owned U.S. patent application Ser. No. 08/056,342 filed Apr. 30, 1993.

The belt 10 also includes a strap 18, a buckle 20 and a torque ring 22. The buckle 20 and torque ring 22 used in the preferred embodiment 10 are disclosed in U.S. Pat. No. 5,036,864, referred to above. Alternatively, the buckle 20 used could be as disclosed in U.S. Pat. No. 5,269,050, the disclosure of which is hereby incorporated by reference. It should be understood that, although preferred, it is not necessary to use a buckle-type fastener to practice the present invention, but that any suitable type of fastener for holding fast the strap 18 could be used.

As described in the aforementioned issued patents, the body 11 of the belt 10 may be made by stitching the binding strip 24 around the edge of the three layer laminated composite structure (i.e., the inner fabric layer 12, the intermediate layer, and the outer fabric layer 16). Thereafter, the strap 18 is stitched to the body 11 over the outer fabric layer 16 with its interior side 18A facing the body 11 and its exterior side 18B facing outwardly, and the various cinching system components are secured to the strap 18 in the manner described below.

The outer fabric layer 16 is preferably a stretchable or expandable fabric, for example a fabric of about 15% Lycra and 85% nylon has been found suitable. "Lycra" is a trademark of E.I. Dupont de Nemours. An example of a material suitable for the outer fabric layer 16 is woven by Milliken Company and bears catalog no. 5 or S/2539. The inner layer 12 is also preferably made from a stretchable or expandable fabric, for example brushed 100% polyester or nylon. The inner layer 12 may provide a brushed tricot or fuzzy texture, for comfort and improved absorbency of perspiration. The layers 12 and 16 are preferably tightly woven webs to provide a closed weave so that when the fabric is not being stretched, i.e., when it is relaxed, there are no open spaces between the threads in the weave of the fabric. The layers 12 and 16 therefore provide a generally solid, unbroken surface.

The intermediate layer may be a yieldable foam elastomer having excellent retentive memory characteristics. It is preferred to make the intermediate foam layer of a closed cell polyethylene foam made by Voltech Division of Sekisui American Corporation of Lawrence, Mass. It is preferably a 4–20 pound "A" grade ¼ inch thick, 100% polyethylene foam known as "Volara". Alternatively, the intermediate layer may be of a different thickness or may be a laminated composite of different foams, for example, a lamination of ⅛" 20 lb. to ⅛" 12 lb. to ⅛" 20 lb. foam layers. These may be laminated together by the "Flame Combining" process described below. The foam material of the intermediate layer 14 is radiation cross linked, as opposed to chemical cross linking. It should be understood, however, that the invention could be applied to a belt body of any construction having the requisite strength and flexibility.

The intermediate and fabric layers are laminated together by any suitable method, such as bonding with a suitable flexible adhesive or by a heat combining technique. One acceptable method is known as "Flame Combining" and is supplied under this identifier by United Foam Plastics Corporation of Georgetown, Mass. In this process, a thin (e.g., 0.050 inches thick) urethane foam layer is first applied to each of the fabric layers 12 and 16 on their surfaces which face the foam layer and the composite is passed over a gas flame bar and into pinch rollers, which laminates the thin foam layers onto the surfaces of the fabric layers. Each fabric/urethane foam lamination is then applied on the respective surface of the intermediate layer with the urethane foam layer facing the intermediate layer and the composite is run over the flame bar and into pinch rollers, for each side. This process is well known in the art as a four pass type in which a first layer is a urethane foam. In the process the urethane foam acts as a bonding agent and any excess largely burns off.

The three laminated layers have their exposed edges bound by the binding strip 24, which may be made of any suitable material such as a nylon ribbon, to make the body 11 of the belt 10. The strip 24 is stitched on in any conventional manner preferably using heavy duty nylon thread. The stitching of the strip 24 is located adjacent to the free edges of the strip 24 and both the inner edge of the strip 24 and the outer edge are stitched in a single pass.

The strap 18 is substantially narrower than the body 11. For example, the strap 18 may typically be approximately 2 inches in width and the body 11 may typically be 4 inches in width, although a wider size may be desirable for applications such as heavy weight lifting usage and a narrower size may be desirable for applications such as aerobics.

The strap 18 is a woven fabric of high strength nylon fibers, is sewn to the body 11 of the belt 10 in between the ends of the strap 18 with stitching extending all the way through the body to the inner surface of the inner layer 12. The strap 18 could be made of any suitably strong and flexible material, such as leather, or any other suitable natural or synthetic material.

The belt 10 differs significantly from belts described in the aforementioned patents because, instead of having the buckle fixed at one of the extreme ends of the strap 18, a power ring 40 is fixed at an extreme end of the strap 18, and the buckle 20 and torque ring 22 are provided on the other end portion. The power ring 40 is fixed at the extreme end of the strap 18 by simply looping end portion 42 of the strap 18 through the power ring 40 and stitching it to itself to close the loop.

As best shown in FIGS. 5 and 6, the buckle 20 and torque ring 22 are secured to the other end portion 44 of the belt 10 by threading the end portion 44 through the torque ring 22 and through slots 20A and 20B of the buckle and stitching the end portion 44 to the body 11 inward of the torque ring 22 and outward of slot 20B. The end portion 44 need not be stitched to the body 11 between the torque ring 22 and the slot 20A, and the stitching outward of slot 20B only extends far enough to secure the buckle 20, for example, approximately 2–3 inches.

A free end 46 of the end portion 44 is an extension of the end portion 44 beyond where the end portion 44 is secured to the body 11. When a user secures the belt 10 around his or her waist, the free end 46 is first inserted through the power ring 40 from the back side of the power ring 40 toward the front side of the power ring 40 so that it loops for approximately 180° around the interior side of bridging portion 48 of ring 40. The free end 46 is then inserted through the buckle 20 and through the torque ring 22 and doubled back on itself by approximately 180° as shown in FIG. 5. The cinching force is then applied as indicated by arrow 56 in FIG. 5. The free end 46 and the strap 18 may be provided with hook and loop type mating fastening patches 47A and 47B to secure the free end to the belt 10 after it is cinched and the buckle 20 closed by rotating tongue 20C to the position shown in FIG. 6.

The power ring 40 may be in the form of an oval ring as illustrated in FIGS. 1–6 with an oval cross section or it may be in the form of a rounded rectangular ring 40A as shown in FIG. 7, which has an oval cross section. In either event, the bridging portion 48 or 48A presents a smooth rounded interior surface 49 or 49A, respectively. The inside surface 49 or 49A (the inside 180° of bridging portion 48 or 48A) is formed with this smooth contour without sharp corners so that the free end 46 may be slid over it with a minimum of frictional resistance. Cross-sectional shapes other than ovals which provide smooth sliding contact with the exterior surface 18B of the free end 46 may also, of course, be used.

The result of using the power ring in conjunction with the torque ring is that the human user may compound the cinching force and to reduce the force which must be held by the fastener while the belt is being worn. When cinching the belt, the user need only exert a force on the end portion 42 which is a fraction of the compression force desired around his or her waist. This construction also reduces the forces which must be held by the buckle 20 for a given tension in the belt 11. In this regard, frictional forces help the buckle to hold the tension in the belt by reducing the tension force which the buckle must hold. The result is that the belt can be adjusted to exert and hold a higher compressive force on the wearer's waist, as is desired in some applications.

Whereas the power rings 40 and 40A as well as the torque ring 22 described above are preferably made from a molded plastic material which is strong and lubricous such as nylon (e.g., Dupont ST801), the power ring and torque ring may be made of other materials. For example, FIGS. 9–13 illustrate a belt 110 of the invention in which the power ring 140 is preferably made of metal, for example steel. In the belt 110, elements corresponding to the elements of the belt 10 are assigned the same reference numbers plus 100.

The construction of the belt 110 is the same as the construction of the belt 10, except as described below. In particular, the power ring 140 includes a closed rectangular ring 150 having a circular cross section and the bridging portion 148 includes a tubular bearing sleeve 152, also having a circular cross section, which envelopes and is rotatable about the bridging shaft 151 of the power ring 140.

As best shown in FIG. 11, the free end 146 bears with its exterior surface for approximately 180° around the inside of the sleeve 152. When the free end 146 is tensioned so as to tighten the belt 110, the sleeve 152 rolls along the exterior surface 118B of the strap 118 and rotates relative to the bridging shaft 151. The sleeve 152 may be lubricated with a grease or oil which is compatible with the materials of the belt to facilitate rotation about shaft 151 when the free end 146 is tightened against it. Also, anti-friction bearings, such as ball or sleeve bearings, could be included between the shaft 151 and sleeve 152 to reduce friction. As in the previously described embodiment, the belt yields a reduction in the force which must be applied to the free end and held by the buckle 120.

For the further reason that the free end 146 must be pulled farther than the closure of the belt 110, the multi-ring construction of the invention is advantageous because it allows redirecting the pulling force on the free end 146 so that it is across the front of the user's body as shown by the arrow 156 in FIG. 11. This could be accomplished using the torque ring 122, as previously described in connection with the belt 10. However, for high tensions it may be preferable to use the construction shown in FIGS. 13 in which a roller ring 160, which is identical in construction to the power ring 140, is secured to the belt 110 by a patch 158. The patch 158 which may be of the same material as the strap 118, but is separate from the strap 118. The patch 158 is looped around leg 161 of the roller ring 160 and secured to the belt 110 by stitching it between the strap 118 and the body 111. After the free end 146 is inserted through the first power ring 140, through the buckle 120 and through the torque ring 122, it is inserted through the roller ring 160 and doubled back on itself by approximately 180° as shown in FIG. 11. The cinching force 156 is thereby exerted in a direction across the front of the body to tighten the belt 110.

A belt of the invention allows cinching a support belt to exert high compressive force on the user's waist. When tightening a belt, the tensioning force exerted on the free end of the belt may be significant and the frictional forces exerted on the free end 146 by the various components of the cinching system may also be significant. These frictional forces result in a net torque being exerted on the belt which tends to rotate the belt about the user's waist.

To counteract the tendency of the belt to rotate about the user's waist when it is being tightened, it is desirable to increase the frictional resistance between the belt and the user's waist. This may be accomplished in a number of ways, one of which is illustrated in FIGS. 9, 14 and 15. It is illustrated that a bead 170 of elastomeric material is deposited in a serpentine pattern on the inside half of the binding strip 124. This can be accomplished before the binding strip 124 is stitched to the belt 110 so that the binding strip 124 may be laid flat as shown in FIGS. 14 and 15 in order to deposit the bead 170, all to one side of the longitudinal center line 172. Any friction increasing material may be used for the bead, and in the preferred embodiment a silicone material is used, for example the material available from Dow Corning™ identified as 3-7044 Textile RTV, Clear. It may also be possible to deposit friction increasing material elsewhere on the inner surface of the body 111, to make the binding strip 124 itself of an elastomeric material, or to make the entire interior surface of the body 111 of an elastomeric material or including portions of an elastomeric material in order to increase the resistance of the belt 110 to turn around a user's waist when it is being tightened. It should also be understood that such measures to prevent the belt from turning around a user's waist when it is being tightened could also be applied to the belt 10, or to the other belts described herein or incorporated by reference.

FIG. 16 illustrates another embodiment 210 of the invention, which has been labelled with the same reference numerals as the belt 10, plus 200. The belt 210 is identical to the belt 10, except that strap 218 is made in two pieces 213 and 215, with the buckle 220 and power ring 240A secured to the belt by strap 213 and the free end 246 is provided by strap 215 which is separate from the strap 213 and stitched to the strap 213 and body 211 at the buckle end at 217, just outside of the torque ring 222. Both straps 213 and 215 may be of the same material as strap 18. This construction has been found to secure buckle 20 better than the construction of the belt 10, since the strap 213 is looped through the slots 220A and 220B for a more secure connection.

FIGS. 17 and 18 illustrate another embodiment 310 of the invention, which has been labelled with the same reference numerals as the belt 10, plus 300. The belt 310 is identical to the belt 10, except as described below.

As in the belt 210, the buckle 320 and power ring 340A in the belt 310 are secured to the belt by a strap 313 and the free end 346 is provided by a strap 315 which is separate from the strap 313, but in the belt 310 the strap 315 is stitched to the strap 313 and body 311 at the power ring end at 317, just outside of the power ring 340A. From where it is stitched to the belt 310 at 317, the free end 346 is looped through a second power ring 341 (identical in construction to the rings 340A and 40A). The second power ring 341 is secured to the buckle end of the belt by a strap 319 which is looped through the second power ring 341 and stitched to the body 311 in the area at 321 and to the strap 313 at 323.

After the free end 346 is looped through the second power ring 341, it is looped through the first power ring 340A, inserted through the buckle 320 and looped through the torque ring 322. It should be understood that any of the torque rings 22, 122, 222 or 322 could be identical in construction to the ring 40A. As shown in FIG. 18, after the buckle 320 is closed, the torque ring 322 may or may not be hooked over the free end of the tongue 320C to keep it closed. If the composite thickness of the strap layers running through the ring 322 interferes with hooking the ring 322 over the tongue 320C, the ring 322 could be made wider.

Preferred embodiments of the invention have been described in detail. Many modifications and variations to the preferred embodiments will be apparent to those of ordinary skill in the art which will incorporate the spirit of the invention. Therefore, the invention should not be limited to the embodiments described, but should be defined by the claims which follow.

I claim:

1. A support belt for cinching around a waist of a human user, comprising:

a strap for surrounding said waist, said strap having an interior surface facing said waist, an exterior surface facing away from said waist, a first end portion and a second end portion opposite from said first end portion, said second end portion having a free end;

a power ring secured to said first end portion, said power ring having an opening therein for receiving said free end therethrough and a bridging portion for contacting said free end on said exterior surface of said strap around approximately 180° of said bridging portion; and a second ring secured to said second end portion of said strap, said second ring having an opening therein for receiving said free end therethrough after said free end is inserted through said power ring and a bridging portion for contacting said free end on said interior surface of said strap around approximately 180° of said bridging portion; and a fastener adapted to releasably secure said free end after said free end has been inserted through said second ring;

wherein said fastener is secured to said second end portion and is positioned between said power ring and said second ring when said belt is secured around said waist to secure said free end between said power ring and said second ring.

2. A support belt as in claim 1, wherein said fastener is secured to said first end portion between said power ring and said second ring along the length of said free end when said free end is threaded through said power ring and said second ring.

3. A support belt as in claim 1, wherein said strap includes at least two separate straps secured together.

4. A support belt as in claim 1, wherein a bridging portion of said power ring includes a sleeve bearing around a shaft, said sleeve bearing contacting said free end and turning about said shaft when said free end is pulled through said power ring.

5. A support belt as in claim 1, wherein said second ring is a torque ring which is adjacent to said fastener and which can be used to lock said fastener closed.

6. A support belt for cinching around a waist of a human user, comprising:

a strap for surrounding said waist, said strap having an interior surface facing said waist, an exterior surface facing away from said waist, a first end portion and a second end portion opposite from said first end portion, said second end portion having a free end;

a power ring secured to said first end portion, said power ring having an opening therein for receiving said free end therethrough and a bridging portion for contacting said free end on said exterior surface of said strap around approximately 180° of said bridging portion; and a second ring secured to said second end portion of said strap, said second ring having an opening therein for receiving said free end therethrough after said free end is inserted through said power ring and a bridging portion for contacting said free end on said interior surface of said strap around approximately 180° of said bridging portion; and a fastener adapted to releasably secure said free end after said free end has been inserted through said second ring;

wherein said fastener is secured to said second end portion and is positioned between said power ring and said second ring when said belt is secured around said waist; and wherein said fastener is a buckle and said free end is inserted through said buckle after said free end is inserted through said power ring but before said free end is inserted through said second ring.

7. A support belt for cinching around a waist of a human user, comprising:

a strap for surrounding said waist, said strap having an interior surface facing said waist, an exterior surface facing away from said waist, a first end portion and a second end portion opposite from said first end portion, said second end portion having a free end;

a power ring secured to said first end portion, said power ring having an opening therein for receiving said free end therethrough and abridging portion for contacting said free end on said exterior surface of said strap around approximately 180° of said bridging portion; and a second ring secured to said second end portion of said strap, said second ring having an opening therein for receiving said free end therethrough after said free end is inserted through said power ring and abridging portion for contacting said free end on said interior surface of said strap around approximately 180° of said bridging portion;

a fastener adapted to releasably secure said free end after said free end has been inserted through said second ring; and a third ring secured to said strap with said second ring between said power ring and said third ring when said free end is threaded through said power ring, second ring and third ring.

8. A support belt as in claim 7, wherein said fastener is secured to said belt between said power ring and said third ring.

9. A support belt for cinching around a waist of a human user, comprising:

a strap for surrounding said waist, said strap having an interior surface facing said waist, an exterior surface facing away from said waist, a first end portion and a second end portion opposite from said first end portion, said second end portion having a free end;

a power ring secured to said first end portion, said power ring having an opening therein for receiving said free end therethrough and a bridging portion for contacting said free end on said exterior surface of said strap around approximately 180° of said bridging portion; and a second ring secured to said second end portion of said strap, said second ring having an opening therein for receiving said free end therethrough after said free end is inserted through said power ring and a bridging portion for contacting said free end on said interior surface of said strap around approximately 180° of said bridging portion;

a fastener adapted to releasably secure said free end after said free end has been inserted through said second ring; and a torque ring which is adjacent to said fastener and which can be used to lock said fastener closed.

10. A support belt as in claim 9, wherein said second ring is a roller ring having an opening therein for receiving said free end therethrough and a bridging portion for contacting said free end on said interior surface of said strap.

11. A support belt as in claim 10, wherein said roller ring includes a sleeve bearing around a shaft, said sleeve bearing contacting said free end and turning above said shaft when said free end is pulled through said roller ring.

12. A support belt for cinching around a waist of a human user, comprising:

a strap for surrounding said waist, said strap having an interior surface facing said waist, an exterior surface facing away from said waist, a first end portion and a second end portion opposite from said first end portion, said second end portion having a free end;

a power ring secured to said first end portion, said power ring having an opening therein for receiving said free end therethrough and a bridging portion for contacting said free end on said exterior surface of said strap around approximately 180° of said bridging portion; and a second ring secured to said second end portion of said strap, said second ring having an opening therein for receiving said free end therethrough after said free end is inserted through said power ring and a bridging portion for contacting said free end on said interior surface of said strap around approximately 180° of said bridging portion;

a fastener adapted to releasably secure said free end after said free end has been inserted through said second ring; and a body secured adjacent to said interior surface of said strap between said first and second end portions, said body having an inner surface which when said belt is in use is adjacent to said waist and wherein said inner surface includes friction material for increasing a coefficient of friction of said surface against said waist;

wherein said body includes a binding strip which is folded longitudinally 180° about its longitudinal axis and sewn around an edge of said body, and said friction material is deposited on said binding strip in an area of said binding strip which is on said inner surface of said belt.

13. A support belt comprising:

a body for encircling a waist of a human user, said body having an interior surface which when said belt is in use is adjacent to said waist;

a cinching system for tightening said body around said waist of said user so as to exert a compressive force on said waist; and friction increasing material on said interior surface of said body having a higher coefficient of friction than other portions of said interior surface of said body so as to increase said resistance of said belt to turning around said waist when said belt is tightened, said friction increasing material being an elastomer which is deposited on said interior surface of said support belt along upper and lower edges thereof.

* * * * *